United States Patent
Smith

(10) Patent No.: US 8,663,263 B2
(45) Date of Patent: Mar. 4, 2014

(54) ACCESS SHEATH WITH BLADE

(75) Inventor: Robert C. Smith, Middletown, CT (US)

(73) Assignee: Covidien LP, Mansfield, MA (US)

( * ) Notice: Subject to any disclaimer, the term of this patent is extended or adjusted under 35 U.S.C. 154(b) by 1259 days.

(21) Appl. No.: 12/124,371

(22) Filed: May 21, 2008

(65) Prior Publication Data

US 2008/0294184 A1 Nov. 27, 2008

Related U.S. Application Data

(60) Provisional application No. 60/931,250, filed on May 22, 2007.

(51) Int. Cl.
*A61B 17/32* (2006.01)

(52) U.S. Cl.
USPC .......................................................... 606/170

(58) Field of Classification Search
USPC ................. 606/184, 185, 167, 170, 172, 174; 600/184; 604/164.01, 264, 506, 604/170.01, 170.02, 239; 473/583, 585
See application file for complete search history.

(56) References Cited

U.S. PATENT DOCUMENTS

| | | | |
|---|---|---|---|
| 3,704,711 A * | 12/1972 | Park | 604/284 |
| 4,963,147 A * | 10/1990 | Agee et al. | 606/170 |
| 5,372,588 A | 12/1994 | Farley et al. | |
| 5,591,186 A * | 1/1997 | Wurster et al. | 606/170 |
| 5,620,456 A * | 4/1997 | Sauer et al. | 606/185 |
| 5,860,996 A | 1/1999 | Urban et al. | |
| 6,077,284 A | 6/2000 | Piraka | |
| 6,187,022 B1 * | 2/2001 | Alexander et al. | 606/185 |
| 6,258,108 B1 * | 7/2001 | Lary | 606/159 |
| 6,270,501 B1 | 8/2001 | Freiberg et al. | |
| 6,296,651 B1 | 10/2001 | Lary et al. | |
| 6,837,874 B1 | 1/2005 | Popov | |
| 2002/0143236 A1 | 10/2002 | Sauer et al. | |
| 2004/0167557 A1 | 8/2004 | Kieturakis et al. | |
| 2007/0260275 A1 * | 11/2007 | Ahlberg et al. | 606/185 |
| 2008/0097504 A1 * | 4/2008 | Datta et al. | 606/185 |

FOREIGN PATENT DOCUMENTS

| | | |
|---|---|---|
| WO | WO 01/21231 A | 3/2001 |
| WO | WO2007/035889 A | 3/2007 |
| WO | WO 2007035889 | 3/2007 |

OTHER PUBLICATIONS

European Search Report for corresponding EP 08251780 date of mailing is Dec. 16, 2008 (3 pages).
European Search Report for corresponding EP 08251780 date of completion is Aug. 28, 2008 (3 pages).
European Search Report dated Aug. 28, 2008, Application No. EP 08 25 1780.

* cited by examiner

*Primary Examiner* — Ryan Severson
*Assistant Examiner* — Katherine M Shi

(57) ABSTRACT

A surgical penetrating system includes a cannula and an obturator. The cannula has an outer wall arranged about a longitudinal axis and a longitudinal opening. At least one substantially linear penetrating member is mounted with respect to the outer wall of the cannula and extends in a general longitudinal direction with respect to the longitudinal axis. The penetrating member is adapted to facilitate passage of the cannula through tissue. Another embodiment of the surgical penetrating system includes a cannula having a longitudinal bore and a penetrating member at least partially and slidably mounted within the longitudinal bore of the cannula. The penetrating member has at least one leg and is axially movable between non-deployed and deployed positions. Moreover, the penetrating member can be mounted for movement relative to the leading end of the cannula and within the longitudinal bore of the cannula between a non-deployed position and a deployed position.

17 Claims, 9 Drawing Sheets

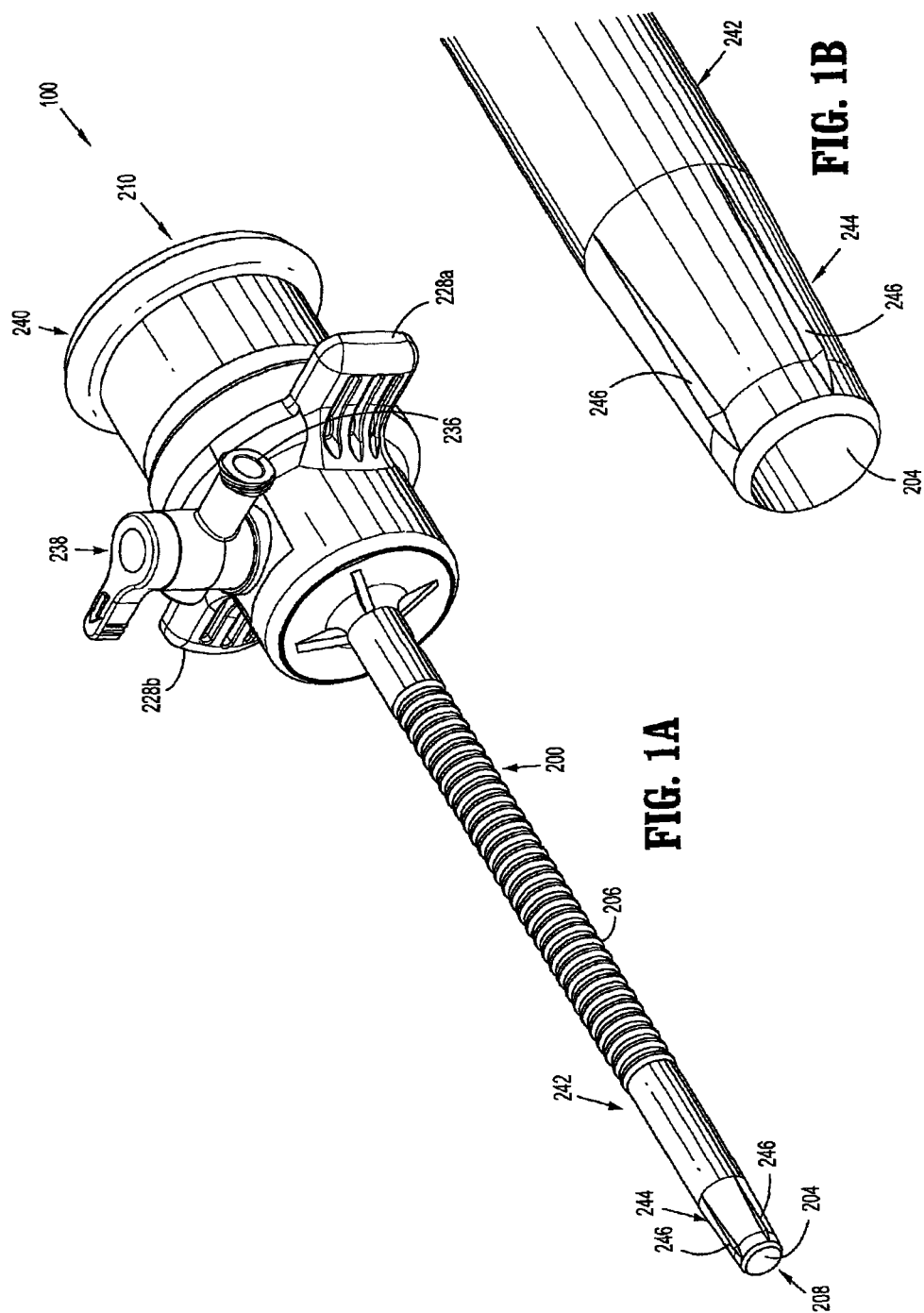

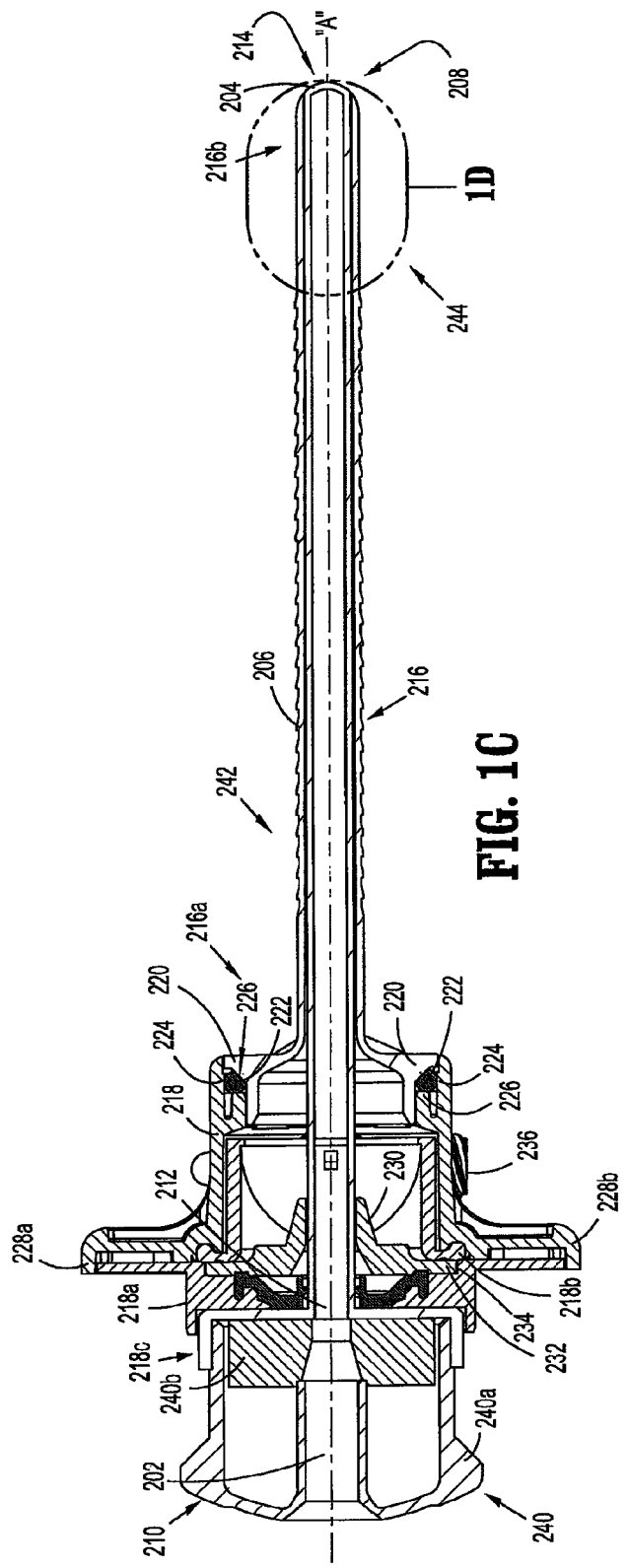

US 8,663,263 B2

ACCESS SHEATH WITH BLADE

CROSS REFERENCE TO RELATED APPLICATION

The present application claims the benefit of and priority to U.S. Provisional Application Ser. No. 60/931,250 filed on May 22, 2007, the entire contents of which are incorporated herein by reference.

BACKGROUND

1. Technical Field

The present disclosure relates to a surgical apparatus for use during minimally invasive surgical procedures such as endoscopic or laparoscopic procedures. More particularly, the present disclosure relates to a penetrating system for accessing a body cavity.

2. Background of the Related Art

Minimally invasive surgical procedures, including endoscopic and laparoscopic procedures, permit surgery to be performed on organs, tissue, and vessels far removed from an opening within the tissue. Laparoscopic procedures are performed in the interior of the abdomen through a small incision such as, for example, a narrow endoscopic tube or cannula inserted through a small entrance incision in the skin. Typically, after the abdominal cavity is insufflated, a trocar is used to puncture the cavity wall, i.e., the peritoneal lining, to create a pathway to the underlying surgical site. Generally, the trocar includes a stylet or obturator having a sharp tip for penetrating the body cavity, which is positioned coaxially within an outer cannula. After penetrating the body tissue with the obturator, the surgeon may remove and leave the outer cannula in place for reception of instrumentation. Surgical instruments can then be introduced into the cannula to perform a surgical procedure. An example of a known trocar is described in commonly assigned U.S. Pat. No. 6,319,266 to Stellon, which issued Nov. 21, 2001, the contents of which are incorporated herein in its entirety by reference.

SUMMARY

The present disclosure is generally directed to further improvements in accessing tissue during endoscopic or laparoscopic surgical procedures. In particular, the present disclosure provides a surgical penetrating system including a cannula defining leading and trailing edges, and an obturator. The cannula has an outer wall arranged about a longitudinal axis and a longitudinal opening. The obturator is configured for insertion within the longitudinal opening of the cannula. At least one substantially linear penetrating member is mounted with respect to the outer wall of the cannula and extends in a general longitudinal direction with respect to the longitudinal axis. Moreover, the penetrating member is adapted to facilitate passage of the cannula through tissue. An embodiment of the presently disclosed surgical penetrating system has a longitudinal slot on the outer wall of the cannula. In this embodiment, at least one penetrating member is mounted for movement relative to the outer wall and within the longitudinal slot between an initial position and an actuated position.

The present disclosure is also directed to a surgical penetrating system including a cannula having a longitudinal bore extending therethrough and a penetrating member at least partially and slidably mounted within the longitudinal bore of the cannula. The cannula defines leading and trailing ends. The penetrating member has at least one leg and is axially movable between non-deployed and deployed positions. Moreover, the penetrating member can be mounted for movement relative to the leading end of the cannula and within the longitudinal bore of the cannula between a non-deployed position and a deployed position. In addition, a distal end of the penetrating member may have a convex structure.

BRIEF DESCRIPTION OF THE DRAWINGS

Embodiments of the present disclosure are described hereinbelow with reference to the drawings, wherein:

FIG. 1A is a perspective view of the surgical penetrating system in accordance with the principles of the present disclosure;

FIG. 1B is a perspective view of the leading penetrating end of the surgical penetrating system in accordance with the embodiment of FIG. 1A;

FIG. 1C is a cross-sectional side view of the surgical penetrating system in accordance with the embodiment of FIG. 1A;

DETAILED DESCRIPTION OF THE EMBODIMENTS

Figure 1D:
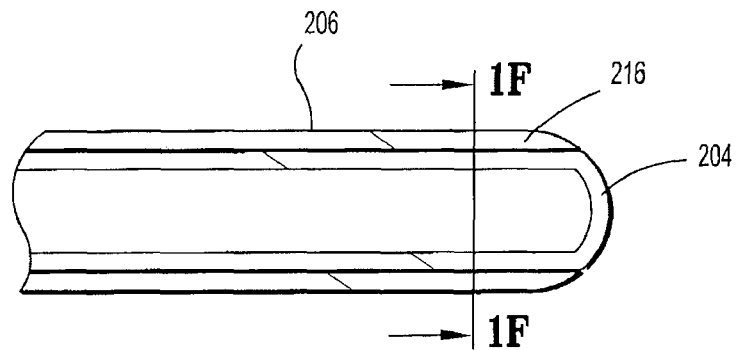
FIG. 1D is an enlarged view of the area of detail 1D indicated in FIG. 1C.

Embodiments of the presently disclosed surgical penetrating system are described in detail with reference to the drawings, in which like reference numerals designate identical or corresponding elements in each of the several views. As used herein and as is traditional, the term "distal" refers to the portion that is farthest from the user and the term "proximal" refers to the portion that is closest to the user. Also, in the specification and the claims, all singular forms, including "a," "an," and "the," include the plural reference unless the context clearly dictates otherwise. Likewise, all plural forms include the singular reference.

Referring initially to FIGS. 1A, 1B, and 1C, a surgical penetrating system is generally designated as reference numeral 100. Surgical penetrating system 100 includes a cannula assembly 200 or any other suitable access device, such as a trocar assembly, capable of accessing a body cavity. Cannula assembly 200 includes an outer wall 206 and defines a leading end 208 and a trailing end 210. As seen in FIG. 1C, cannula assembly 200 additionally includes a longitudinal opening or passageway 202 allowing introduction of many kinds of surgical instruments therethrough. Due to its high operational flexibility, cannula assembly 200 can be used to perform numerous surgical procedures. For instance, surgeons can employ cannula assembly 200 to perform laparoscopic surgery. During laparoscopic surgery, doctors insufflate a peritoneal cavity with a suitable gas, such as carbon dioxide, to raise the cavity wall from the internal organs therein. In such procedures, surgeons can effectively use cannula assembly 200 to access and insufflate the peritoneal cavity.

In addition to cannula assembly 200, surgical penetrating system 100 can also include an obturator assembly 204 slidably positioned within the longitudinal opening 202 of the cannula assembly 200, as illustrated in FIG. 1C. Accordingly, obturator assembly 204 is configured for insertion within the longitudinal opening of the cannula assembly 200. Obturator assembly 204 defines a proximal end 212 and a distal end 214. Although the drawings show a blunt distal end 214, the distal end 214 of obturator assembly 204 can be a sharp pointed instrument. The present disclosure further contemplates that distal end 214 of obturator assembly 204 may have any suitable shape, form, or structure. Moreover, the distal end 214 of obturator assembly 204 can be adapted to allow visualization therethrough. In operation, surgeons may use the obturator assembly 204 to facilitate introduction of the cannula assembly 200 within the abdominal cavity or any other body cavity. Once access to a body cavity has been achieved, the obturator assembly 204 can be removed from the cannula assembly 200 to permit subsequent introduction of surgical instrumentation through the cannula assembly 200.

Cannula assembly 200 further includes a cannula sleeve 216 and a cannula housing 218. Cannula sleeve 216 has a proximal end 216a and a distal end 216b and defines a longitudinal axis "A" extending along a length thereof. Outer walls 206 of cannula assembly 200 are arranged about the longitudinal axis "A." Cannula sleeve 216 also defines the longitudinal opening 202. As discussed above, longitudinal opening 202 is adapted to allow passage of surgical instrumentation therethrough. Stainless steel or other suitable rigid materials, such as a polymer or the like, may be used to make cannula sleeve 216. The material of construction of cannula sleeve 216 can be clear or opaque. The diameter of cannula sleeve 216 can significantly vary. In one embodiment, for example, the diameter of sleeve 216 ranges from about 3 millimeters to about 15 millimeters. Additionally, cannula sleeve 216 includes a flange 220 formed at its distal end 216a.

Cannula housing 218 is connected to flange 220 of cannula sleeve 216. In one embodiment, this connection is achieved through ultrasonic welding, adhesives, cements, etc. Alternatively, the cannula housing 218 and flange 220 can be connected to each other through a bayonet, or a threaded or snap-fit coupling. Nonetheless, it is envisioned that cannula housing 218 and flange 220 of cannula sleeve 216 can be coupled to each other by any suitable coupling apparatus or mechanism. An O-ring 222 can be disposed between an interior bearing surface 224 of cannula housing 218 and an exterior bearing surface 226 of flange 220 to minimize leakage of gases between the cannula housing 218 and flange 220 during use.

Several components can form cannula housing 218. Altogether, cannula housing 218 can have a bell-shaped structure or any other suitable shape, structure, or form. Alternatively, a single component can monolithically form cannula housing 218. In the depicted embodiment, cannula housing 218 includes several inner components 218a and outer components 218b connected together. The outer components 218b of cannula housing 218 may serve different purposes. An embodiment of cannula housing 218, for instance, includes first and second finger tabs 228a, 228b to facilitate grasping by a user. First and second finger tabs 228a, 228b are arranged in a diametrical opposed relation and are configured to receive the fingers of a user.

As discussed above, cannula housing 218 can also include several internal components 218b. In one embodiment, cannula housing 218 includes a resilient valve 230 disposed therein. Resilient valve 230 includes a circumferential flange 232 resting on an internal ledge 234 of cannula hosing 218. During operation, resilient valve 230 closes in the absence of a surgical instrument or in response to the pressurized environment of the insufflation gases present in the body cavity. Resilient valve 230 can be a duckbill valve, a flapper valve, or any other suitable device. Irrespective of the specific kind of valve employed, resilient valve 230 responds to the pressure conditions of the insufflation gasses in the body cavity.

A source of insufflation gases supplies cannula assembly 200 with fluids through a port 236. Port 236 is connected to a stop valve 238 and is in fluid communication with longitudinal opening 202. Stop valve 238 can move between open and closed positions. While the stop valve 238 is in its open position, fluids from the external source of insufflation gases can access longitudinal opening 202. Conversely, in its closed position, stop valve 238 obstructs the fluid communication between the external source of insufflation gases and the longitudinal opening 202.

To prevent leakage of insufflation gases, cannula housing 218 includes a seal assembly 240 releasably connected to the proximal end 218c of cannula housing 218. Seal assembly 240 includes a seal housing 240a and an internal air-tight seal 240b. Internal seal 240b is disposed within seal housing 240a and can have any suitable shape. A flat disc-shaped, conical or hourglass shaped member can form internal seal 240b. Aside from its overall shape, internal seal 240b can include a constriction or closure.

Internal seal 240b can be formed of any suitable material. In one embodiment, internal seal 240b is made of a fabric material molded with an elastomer. Alternatively, internal seal 240b is only made of fabric. The fabric employed to form internal seal 240b can be a woven material, a braided material, or a knitted material. In particular, internal seal 240b can be made of a nylon sold under the trademark KEVLAR by E.I. DuPont de Nemours and Company. In practice, internal seal 240b can be made of any material configured to expand and compress about a surgical instrument inserted therethrough. In any case, the material employed should minimize the formation of gaps when a surgical instrument in introduced into the internal seal 240b. Internal seal 240b, for instance, can be formed of a porous material. In such case, a gas impermeable coating should cover at least a portion of internal seal 240b. A gas impermeable coating, however, would not necessarily enhance the capabilities of an internal seal 240b made of gas impermeable material. Further still, another kind of coating can cover an interior section of internal seal 240b to facilitate passage of an instrument through internal seal 240b. This coating can be made of urethane, silicon or any other flexible lubricious material.

Internal seal 240a, as discussed hereinabove, can include a constriction or closure. This constriction or closure can be formed by twisting the fabric of internal seal 240b about longitudinal axis "A." Alternatively, the fabric can be constructed or arranged so that the fabric itself forms a constriction or closure. Further still, internal seal 240b can be molded so as to have a constriction. The present disclosure, however, contemplates internal seals 240b having other suitable structural arrangements. For example, internal seal 240b can be knitted, braided, or woven. The seals disclosed in certain embodiments of commonly assigned U.S. Pat. No. 6,482,181 and U.S. patent application Ser. No. 11/406,922, the entire disclosures of which are hereby incorporated by reference herein, can be employed with cannula assembly 200.

Referring now to FIGS. 1B, 1C, 1D, 1E, and 1F, the cannula sleeve 216 of cannula assembly 200 has a main section 242 and a generally tapered section 244 located adjacent to the leading end 208 of the cannula assembly 200. The tapered section 244 includes at least one penetrating member 246 disposed thereon. Although the drawings show a tapered section 244 including four penetrating members 246, the present disclosure contemplates that cannula assembly 200 can include fewer or more penetrating members 246. In particular, penetrating members 246 are mounted with respect to the outer wall 206 of cannula assembly 200 and are configured to provide cannula assembly 200 with penetrating capabilities thus obviating the need for a separate piercing device introduced within cannula sleeve 216. Accordingly, penetrating members 246 are adapted to penetrate body tissue, thereby facilitating passage of the cannula through tissue. Penetrating members 246 can incorporate structure to separate, retract, dissect, cut, puncture, pierce, or penetrate body tissue. Cutting edges, blades, and points are among the possible structures that can be incorporated with penetrating member 246.

Figure 1E:
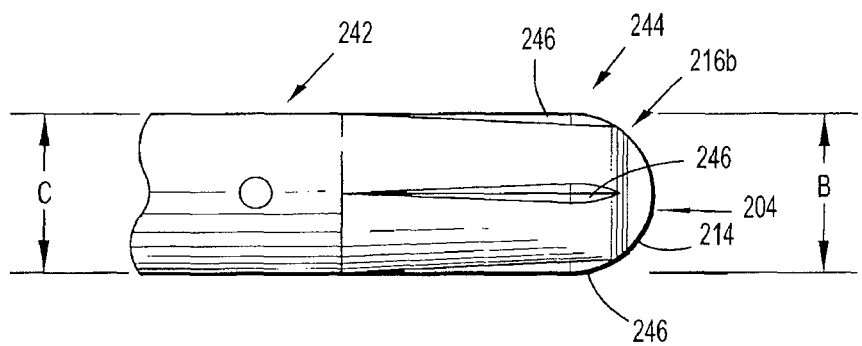
FIG. 1E is a side plan view the leading penetrating end of the surgical penetrating system in accordance with the embodiment of FIG. 1A.
Figure 1F:
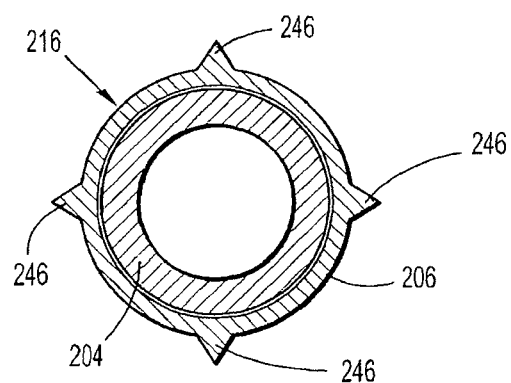
FIG. 1F is a cross-sectional view of the surgical penetrating system in accordance with the embodiment FIG. 1A taken along section lines 1F-1F of FIG. 1D.

Penetrating members 246 are substantially linear and extend in a general longitudinal direction with respect to longitudinal axis "A." The present disclosure, however, envisions that penetrating members 246 may have other suitable shapes, structures, or configurations. In one embodiment, as shown in FIG. 1B and 1E, penetrating members 246 are radially spaced about the outer wall 206 of cannula assembly 200. Tapered section 244 of cannula assembly 200 includes a first pair and a second pair of penetrating members 246. Each pair of penetrating members 246 is arranged in a general diametrical opposed relation, as seen in FIG. 1F. Tapered section 244 defines an effective transverse dimension "B" inclusive of one pair of penetrating members 246, as illustrated in FIG. 1E. Transverse dimension "B" generally approximates a corresponding transverse dimension "C" of the main section 242 of cannula assembly 200. This structural arrangement may facilitate the introduction of cannula assembly 200 and obturator assembly 204 into a body cavity.

As shown in FIG. 1E, the distal end 214 of obturator assembly 204 extends beyond the distal end 216b of cannula sleeve 216. Obturator assembly 204 may be comprised of a polymeric material. A polymeric obturator assembly 204 can be manufactured with known injection molding techniques. Obturator assembly 204 can alternatively be made of optical glass. Regardless of the material used to construct obturator assembly 204, the distal end 214 of obturator assembly 204 may have a transparent window that allows visualization along the longitudinal axis "A" of cannula sleeve 216 and locations offset relative to the longitudinal axis "A." Light, with or without clear imaging capabilities, may pass through distal end 214 of obturator assembly 204.

Figure 2A:
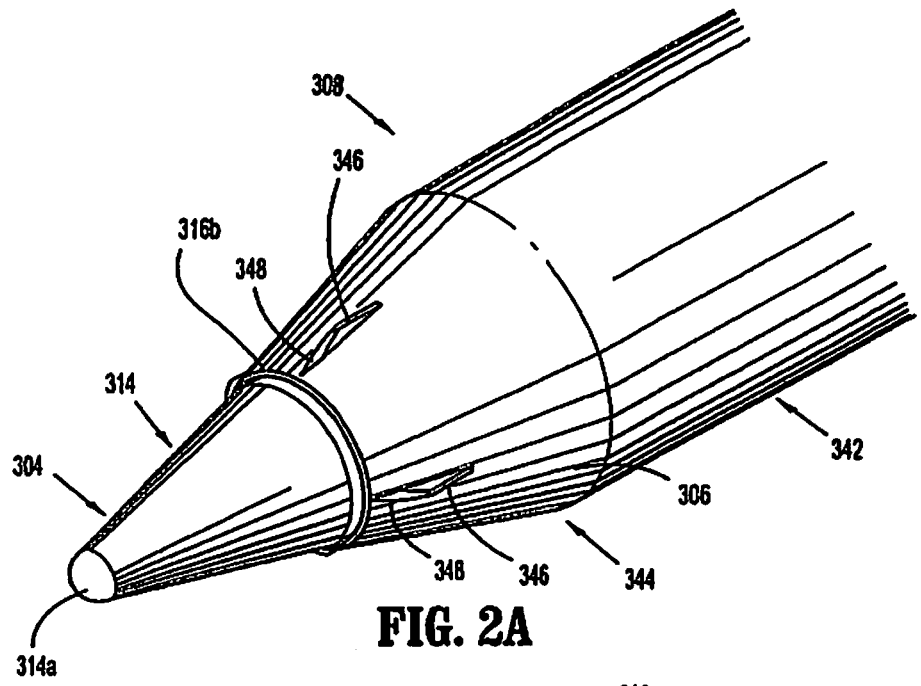
FIG. 2A is a perspective view of the leading penetrating end of a surgical penetrating system illustrating a plurality of penetrating members mounted in longitudinal slots in accordance with an alternate embodiment of the present disclosure.
Figure 2B:
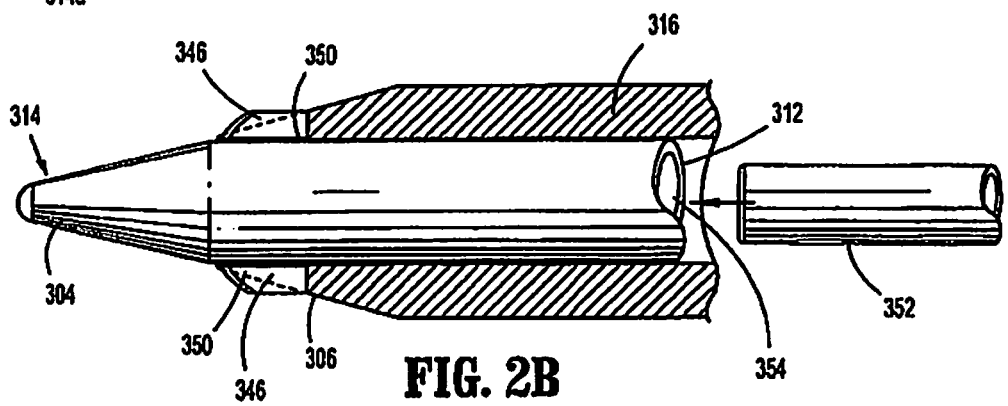
FIG. 2B is a side cross-sectional view of the leading penetrating end of the surgical penetrating system in accordance with the embodiment of FIG. 2A.
Figure 2C:
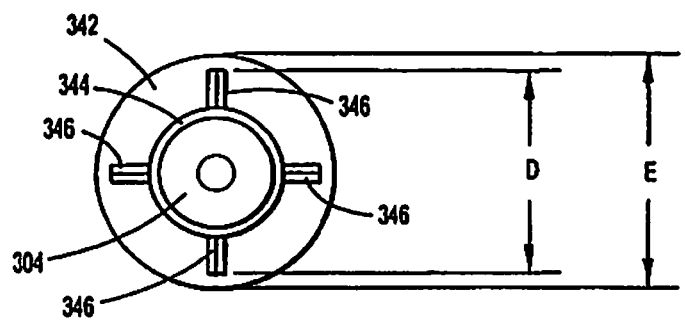
FIG. 2C is an axial view of the surgical penetrating system in accordance with the embodiment of FIG. 2A.

In an alternate embodiment, as depicted in FIGS. 2A, 2B, and 2C, cannula assembly 300 includes a cannula sleeve 316 having a main section 342 and a tapered section 344 located at a leading end 308 of cannula assembly 300. Additionally, cannula assembly 300 has an outer wall 306 that extends throughout the length of the cannula assembly 300. Outer wall 306 of cannula assembly 300 includes at least one longitudinal slot 348 disposed thereon. An embodiment of the presently disclosed cannula assembly 300 includes four longitudinal slots 348 disposed on the tapered section 344 of cannula sleeve 316. Longitudinal slots 348 are adapted to receive at least a portion of penetrating members 346. In this embodiment, cannula assembly 300 includes two pairs of penetrating members 346 and two pairs of longitudinal slots 348. The pairs of penetrating members 346 and its corresponding longitudinal slots 348 are arranged in a diametrical opposed relation. Each penetrating member 346 is disposed on an inner portion 350 of cannula sleeve 316 and extends through longitudinal slots 348 beyond outer wall 306 of cannula assembly 300. Tapered section 344 defines an effective transverse dimension "D" inclusive of one pair of penetrating members 346, as illustrated in FIG. 2C. Main section 344 of cannula assembly 300 also defines a transverse dimension "E." Transverse dimension "E," however, is larger than transverse dimension "D."

Cannula assembly 300 additionally includes an obturator assembly 304 positioned within cannula sleeve 316. Obturator assembly 304 has a proximal end 312 and a distal end 314. In the embodiment illustrated in FIG. 2B, the distal end 314 of obturator assembly 304 has a tapered configuration and a tip 314a. Tip 314a may be blunt or sharp. The distal end 314 of obturator assembly 304 extends beyond the distal end 316b of cannula sleeve 316. Obturator assembly 304 may be made of a polymeric material, optical glass, or any other suitable material. In one embodiment, the distal end 214 of obturator assembly 304 has a transparent window that allows visualization along the longitudinal axis "A" of cannula sleeve 216 and locations offset relative to the longitudinal axis "A." Light, with or without clear imaging capabilities, may pass through distal end 314 of obturator assembly 204. During use, surgeons may introduce an optical instrument or endoscope 352 through a bore 354 of obturator assembly 304, as shown in FIG. 2B. One suitable endoscope is disclosed in commonly assigned U.S. Pat. No. 5,634,881 to Francis, the entire contents of which is incorporated herein by reference.

In still another embodiment, cannula assembly 400 includes a cannula sleeve 416 having a main section 442 and a tapered section 444 disposed on the leading end 408 of cannula assembly 400. Cannula sleeve 416 has an outer wall 406 extending throughout a length thereof and at least one longitudinal slot 448. Longitudinal slots 448 are configured to receive at least a portion of a penetrating member 446 and have an elongate structure. The elongate structure of longitudinal slots 448 defines a trailing end 448a and a leading end 448b. The leading end 448b of longitudinal slot 448b corresponds with a distal end 416b of cannula sleeve 416. Thus, while the trailing end 448a of longitudinal slot 448 is partially enclosed, the leading end 448b has an opening that allows penetrating members 446 to move beyond the confines of cannula sleeve 416.

Penetrating members 446 are disposed within sleeve 416 and are configured to provide cannula assembly 400 with penetrating capabilities. Accordingly, penetrating members 446 are adapted to penetrate body tissue, thereby facilitating passage of the cannula assembly 400 through tissue. Penetrating members 446 may incorporate structure to separate, retract, dissect, cut, puncture, pierce, or penetrate body tissue. Cutting edges, blades, and points are among the possible structures that can be incorporated with penetrating member 446. In the depicted embodiment, penetrating member 446 has a blade 446c positioned at its distal end 446d.

With reference to FIGS. 3B, 3C, 3D, and 3E, a link 452 can be slidably connected to each penetrating member 446. Actuation links 452 are disposed within cannula sleeve 416 and are each connected to cam pin 452a. A portion of each actuation link 452 is slidably disposed in a longitudinal slot 446a of penetrating member 446. Longitudinal slot 446a of penetrating member 446 is configured to slidably hold actuation link 452 or any other suitable actuation apparatus. Penetrating member 446 is pivotably connected within sleeve 416. A pivot pin 454 pivotably interconnects cannula sleeve 416 and penetrating member 446. Penetrating member 446 includes a hole 446b adapted to receive pivot pin 454. Nevertheless, the present disclosure contemplates that other suitable fastening members could be used to pivotably interconnect penetrating member 446 and cannula sleeve 416.

Figure 3A:
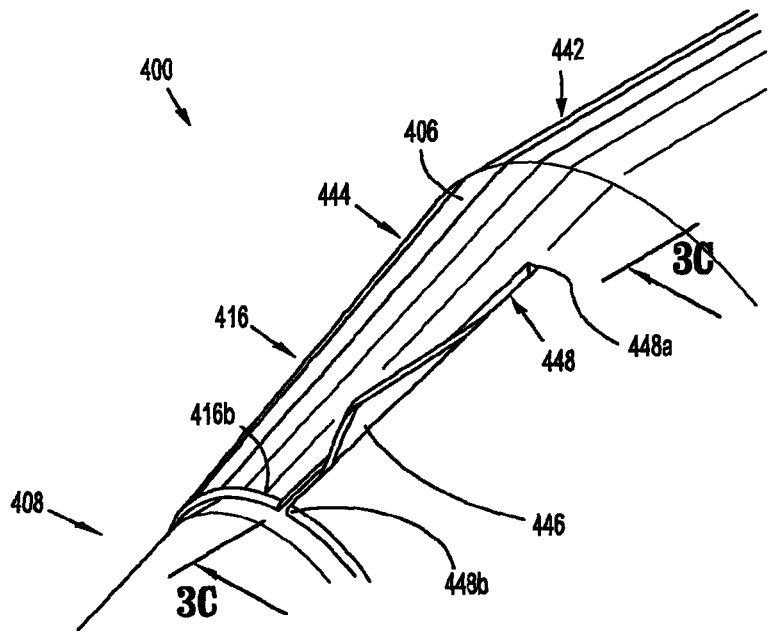
FIG. 3A is an enlarged perspective view of a leading penetrating end of a surgical penetrating system, illustrating at least one penetrating member mounted for movement relative to an outer wall of a cannula in accordance with an alternate embodiment of the present disclosure.
Figure 3B:
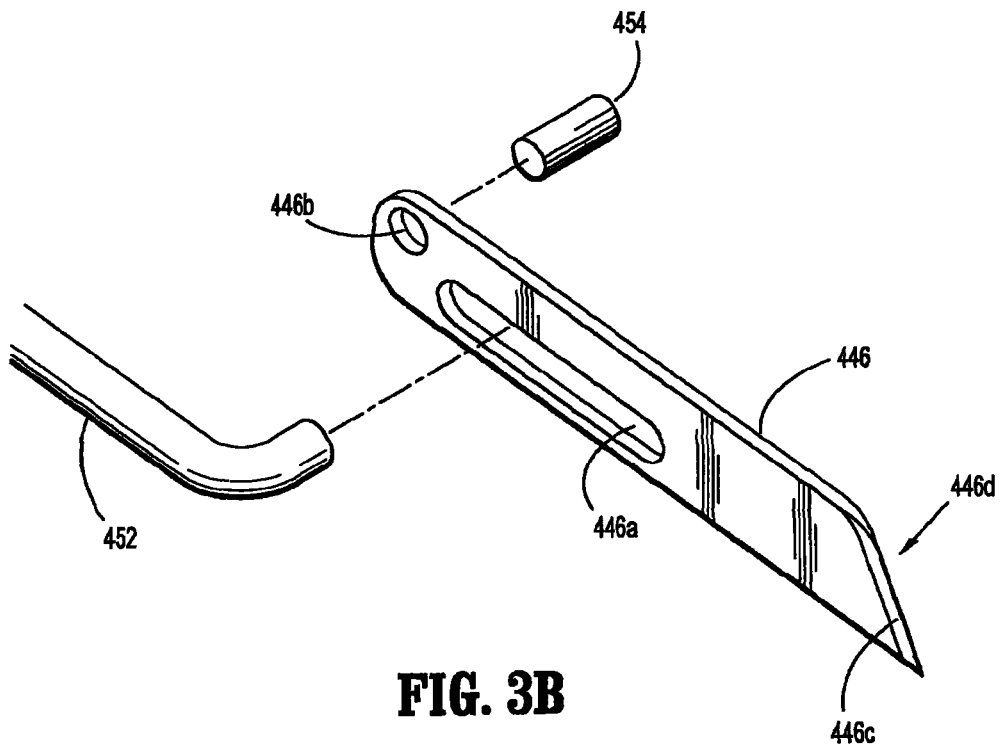
FIG. 3B is perspective view of a penetrating member, an actuation link, and a pivot pin of the surgical penetrating system in accordance with the embodiment of FIG. 3A.
Figure 3C:
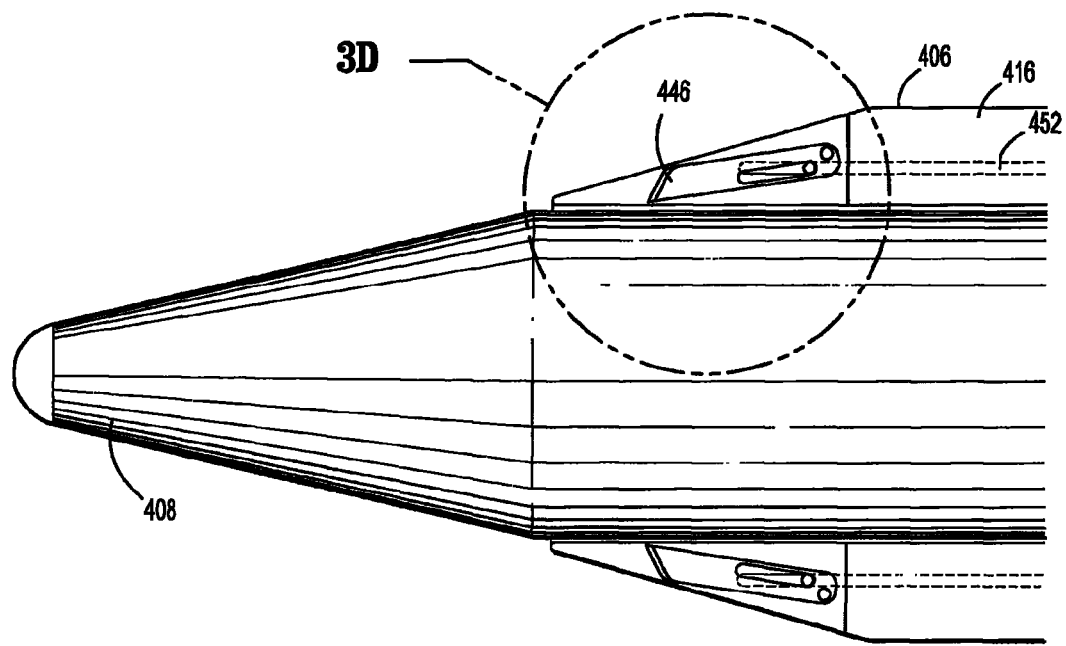
FIG. 3C is a side plan view of the leading penetrating end of the surgical penetrating system in accordance with the embodiment of FIG. 3A.
Figure 3D:
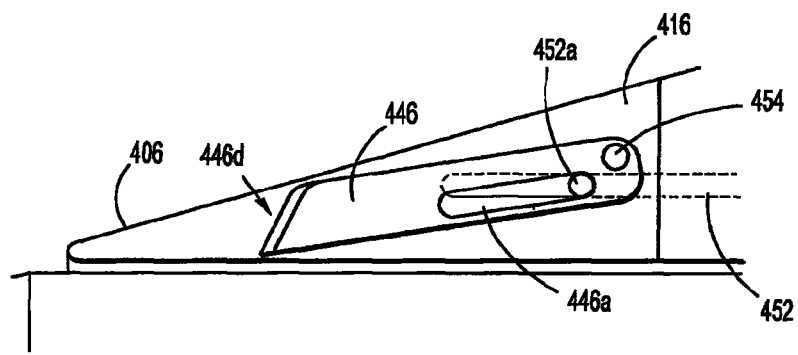
FIG. 3D is an enlarged view of the area of detail 3D indicated in FIG. 3C illustrating a penetrating member in a non-deployed position.
Figure 3E:
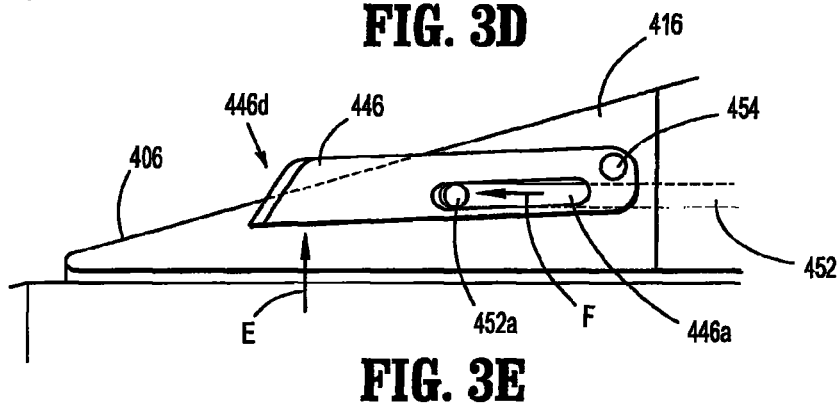
FIG. 3E is a similar view to the view of FIG. 3D illustrating the penetrating member in a deployed position in accordance with the embodiment of FIG. 3A.

Penetrating members 446 are mounted for movement relative to the outer wall 406 of cannula sleeve 416 and within the longitudinal slot 448 of the cannula sleeve 416 between an initial position and an actuated position. Link 452 is adapted to move at least one penetrating member 446 between initial and an actuated positions, as seen in FIGS. 3D and 3E, respectively. During operation, penetrating members 446 are initially positioned at least partially within cannula sleeve 416. To place penetrating members 446 in the actuated position, a user distally translates actuation links 452 along longitudinal slots 446a of penetrating members 446 in the direction indicated by arrow "F." In response to the translation of actuation link 452, cam pin 452a attached to actuation link 452 traverses longitudinal slot 446a of penetrating member 446, thereby causing penetrating members 446 to pivot clockwise about their respective pivot pins 454 through the camming mechanism effected through cam pins 452a and longitudinal slots 446a. As penetrating members 446 pivots, the distal ends 446d of penetrating members 446 move upwardly to the actuated position in a direction indicated by arrow "E." Once penetrating members 446 are deployed, a surgeon may use cannula assembly 400 to penetrate body tissue. Users can return penetrating members 446 to their initial position by moving actuation links 452 in a proximal direction. Any suitable actuation mechanism or device can be used to move actuation links 452. Actuation links 452 may be individually deployable, or, in the alternative, connected to a single actuator and simultaneously deployed by the clinician.

Figure 4A:
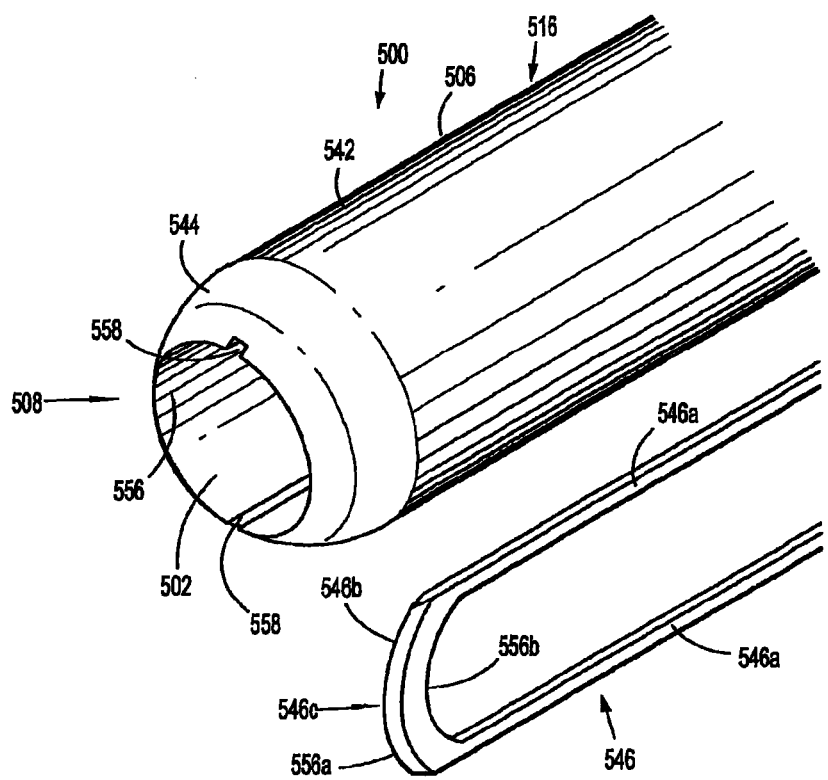
FIG. 4A is a perspective view of a cannula and a penetrating member of a surgical penetrating system in accordance with an alternate embodiment of the present disclosure.
Figure 4B:
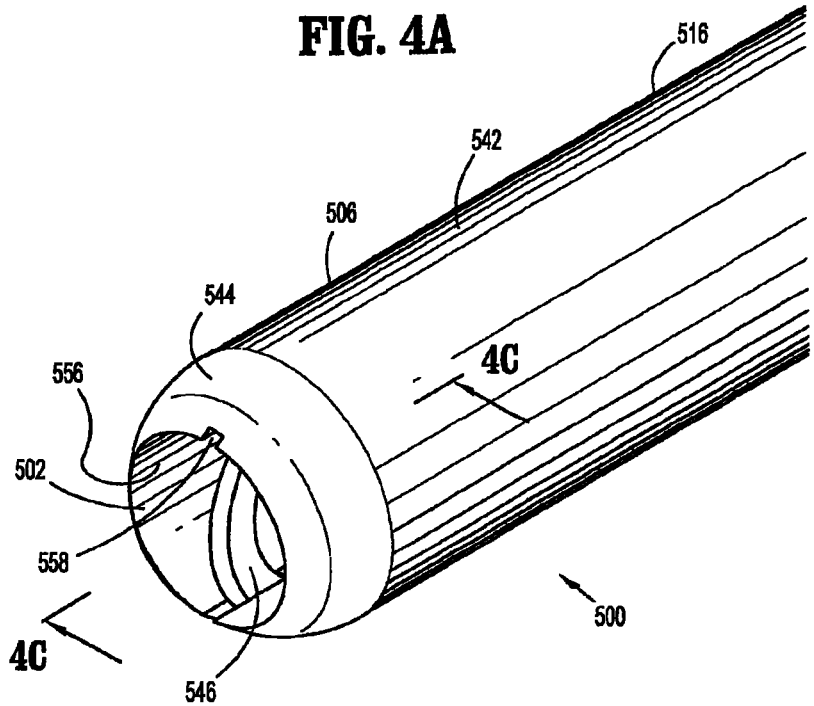
FIG. 4B is perspective view of the surgical penetrating system with the penetrating member slidably mounted within a longitudinal bore of the cannula in accordance with the embodiment of FIG. 4A.

With reference to FIGS. 4A and 4B, another embodiment of the presently disclosed penetrating system 100 is illustrated. Cannula assembly 500 includes a cannula sleeve 516 having a main section 542 and a tapered section 544 disposed on a leading end 508 of cannula assembly 500. In addition to cannula sleeve 516, cannula assembly 500 includes a longitudinal bore 502 extending therethrough.

Cannula sleeve 516 has an outer surface 506 and an inner surface 556. Both inner surface 556 and outer surface 506 extend throughout the length of sleeve 516. At least one longitudinal slot 558 is disposed on inner surface 556. Longitudinal slot 558 is adapted to receive at least one leg 546a of a penetrating member 546. In the illustrated embodiment, cannula assembly 500 includes two longitudinal slots 558 positioned in a diametrical opposed relation.

As discussed hereinabove, cannula assembly 500 also includes a penetrating member 546 having at least one leg 546a. The embodiment depicted in FIG. 4A includes a penetrating member 546 with two legs 546a. Penetrating member 546 is disposed in longitudinal bore 502 and is configured to provide cannula assembly 500 with penetrating capabilities. Accordingly, penetrating member 546 is adapted to penetrate body tissue, thereby facilitating passage of the cannula assembly 500 through tissue. Penetrating member 546 may incorporate structure to separate, retract, dissect, cut, puncture, pierce, or penetrate body tissue. Cutting edges, blades, and points are among the possible structures that can be incorporated with penetrating member 546. In the depicted embodiment, a penetrating member 546 has a blade 546b positioned at a distal end 546c thereof. Blade 546b includes a distal surface 556a having a convex structure and a proximal surface 556b having a concave structure, as illustrated in FIG. 4A. Legs 546a of penetrating member 546 extend proximally from blade 546b.

Figure 4C:
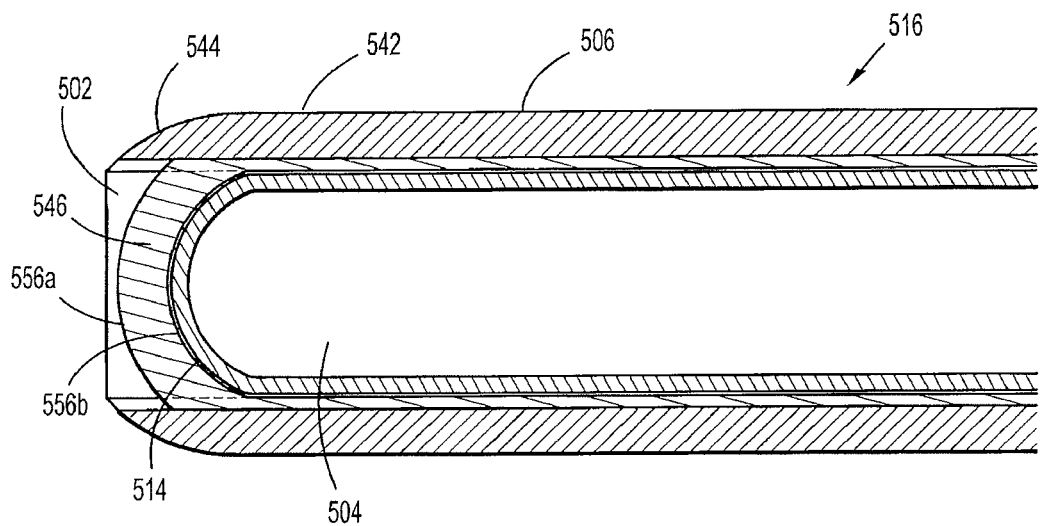
FIG. 4C is a cross-sectional view of the leading penetrating end of the surgical penetrating system in accordance with the embodiment of FIG. 4A, taken along section lines 4C-4C.
Figure 4D:
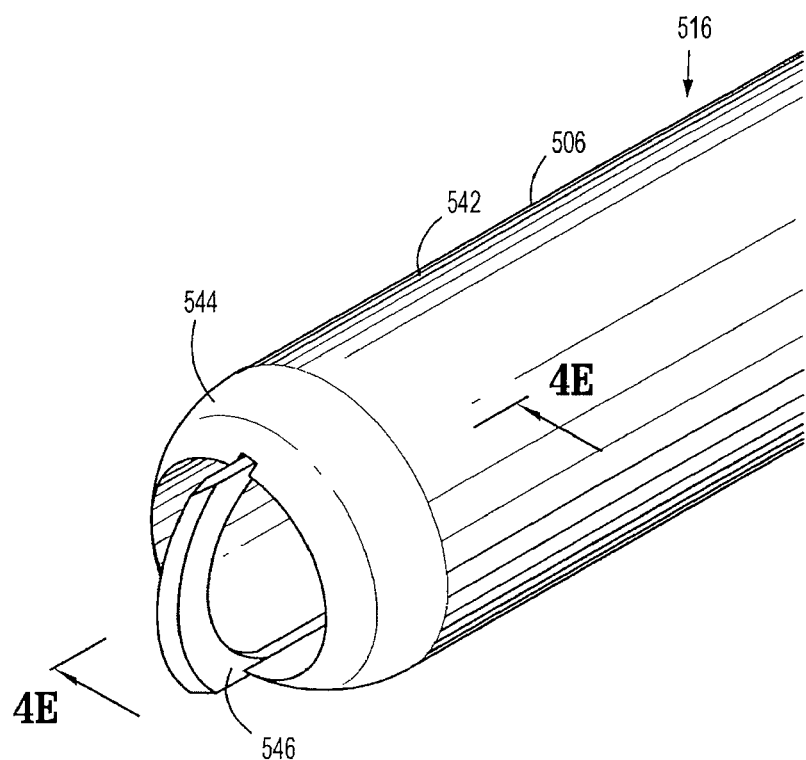
FIG. 4D is a perspective view of the leading penetrating end of the surgical penetrating system in accordance with the embodiment of FIG. 4A.
Figure 4E:
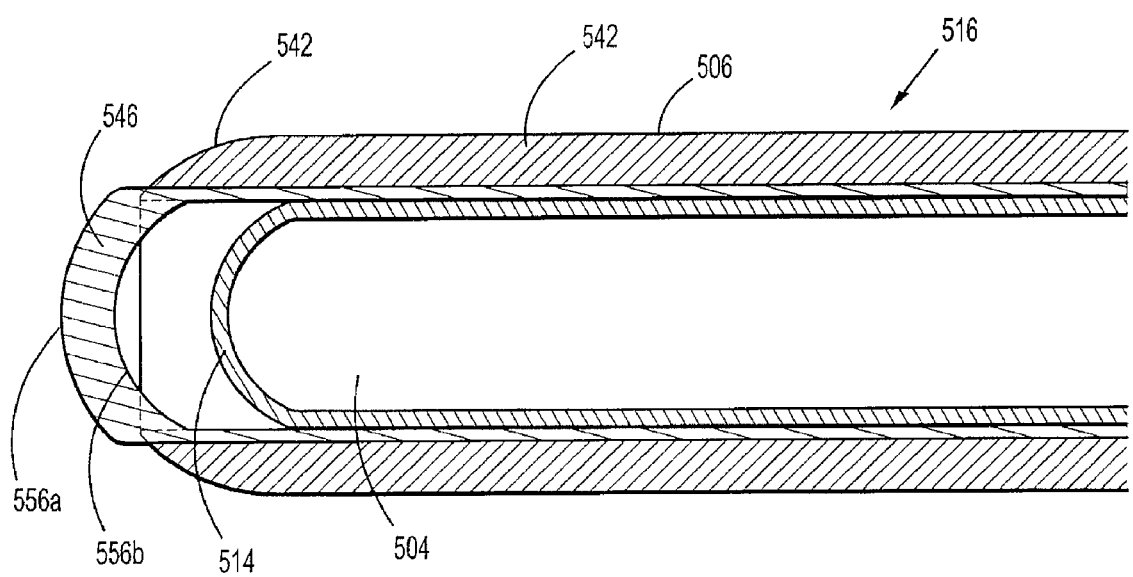
FIG. 4E is a cross-sectional view of the leading penetrating end of the surgical penetrating system in accordance with the embodiment of FIG. 4A, taken along section lines 4E-4E of FIG. 4D.

Referring to FIGS. 4C, 4D, and 4E, an obturator assembly 504 can be slidably positioned in longitudinal bore 502 of cannula sleeve 516. Accordingly, obturator assembly 504 is configured for insertion within the longitudinal bore 508 of cannula sleeve 516. In one embodiment, obturator assembly 504 includes a blunt distal end 514 having a convex structure. The proximal surface 556b of blade 546 structurally corresponds with the distal end 514 of obturator assembly 504. The present disclosure nevertheless envisions that obturator assembly 504 may have any suitable structure or configuration. Also, the distal end 514 of obturator assembly 504 can be adapted to allow visualization therethrough. In a further alternate obturator assembly 504 is an endoscope including an optical train and illumination system as disclosed in the aforementioned Francis '881 patent.

Penetrating member 546 is mounted for movement relative to the leading end 508 of the cannula assembly 500 and within the longitudinal bore 502 of the cannula sleeve 516 between non-deployed and deployed positions. In the non-deployed position, penetrating member 546 is at least partially disposed within the longitudinal bore 502, as illustrated in FIG. 4C. An operator may move penetration member 546 to a deployed position by translating at least one leg 546a distally, as shown in FIGS. 4D and 4E. During this translation, legs 546a slides along longitudinal slot 558 of inner surface 556 to deploy penetrating member 546. Once penetrating member 546 is deployed, a surgeon may introduce cannula assembly 500 into a body cavity by penetrating tissue. A user may return penetrating member 546 to its non-deployed position by sliding at least one leg 546a proximally. Penetrating system 100 may incorporate any suitable actuating device or mechanism to move penetrating member 546. For example, penetrating member 546 may be operatively connected obturator assembly 504 at respective proximal or trailing ends via conventional coupling means whereby advancement and retracting of obturator assembly 504 causes corresponding movement of penetrating member 546.

Surgical penetrating system 100 can use any of the cannula assemblies described above. In the interest of brevity, the present disclosure will only describe the method for using one embodiment of the presently disclosed surgical penetrating system 100. The methods for using the previously described cannula assemblies are substantial similar. Any differences between such methods will be explained herein.

In use, a body cavity, e.g, abdominal cavity, is insufflated to raise the cavity wall, thereby providing greater access to tissue and organs. Penetrating system 100 is assembled with the obturator positioned within cannula assembly 200. A small incision optionally may be made by the clinician within the abdominal cavity. The leading penetrating end of the system is placed within the incision. The surgeon then translates cannula assembly 200 distally to penetrate the body tissue to establish a port of entry. If the surgeon uses cannula assemblies 400 or 500, the surgeon should deploy the penetrating members 446 or 546 before moving cannula assembly 400 or 500 distally. Thereafter, the doctor continues the distal translation of the cannula assembly 200 to reach the desired surgical site. Once the surgeon positions the leading end 208 of cannula assembly 200 in the desired position, the surgeon discontinues the distal movement of cannula assembly 200. The surgeon may then remove obturator assembly 204 from cannula assembly 200 and introduce surgical instrumentation through cannula assembly 200 to perform a surgical procedure.

It will be understood that various modifications can be made to the embodiments disclosed herein. Therefore, the above description should not be construed as limiting, but merely as exemplifications of the embodiments. Those skilled in the art will envision other modifications within the scope and spirit of the claims appended hereto.

What is claimed is:

1. A surgical penetrating system for accessing tissue, comprising:
    a cannula including an outer wall arranged about a longitudinal axis and having a longitudinal opening, the cannula defining leading and trailing ends, the outer wall having an inner surface and an outer surface and including at least one wall slot defined therein;
    at least one penetrating member mounted to the outer wall of the cannula, the at least one penetrating member adapted to move within the wall slot between an initial position and an actuated position, wherein in the initial position the at least one penetrating member is maintained entirely between the inner surface and the outer surface of the outer wall of the cannula and in the actuated position the at least one penetrating member extends through the wall slot to thereby facilitate passage of the cannula through tissue.

2. The surgical penetrating system according to claim 1, wherein the at least one penetrating member is adjacent the leading end of the cannula.

3. The surgical penetrating system according to claim 2, including a plurality of penetrating members and corresponding wall slots radially spaced about the outer wall of the cannula.

4. The surgical penetrating system according to claim 1, including an obturator positionable within the longitudinal opening of the cannula, the obturator adapted to permit visualization therethrough.

5. The surgical penetrating system according to claim 1, wherein the cannula includes a main section and a generally tapered section adjacent the leading end of the cannula.

6. The surgical penetrating system according to claim 5, including a pair of penetrating members disposed on the tapered section of the cannula.

7. The surgical penetrating system according to claim 6, including first and second pairs of penetrating members and corresponding first and second slots, the penetrating members of each of the first and second pairs being arranged in a general diametrical opposed relation.

8. The surgical penetrating system according to claim 6, wherein the penetrating members of the pair are arranged in general diametrical opposed relation, and wherein the tapered section defines an effective transverse dimension inclusive of the pair of the penetrating members and transverse to the longitudinal axis, the transverse dimension generally approximating a corresponding transverse dimension of the main section of the cannula.

9. The surgical penetrating system according to claim 1, wherein the at least one penetrating member is pivotably attached to the outer wall of the cannula, the at least one penetrating member adapted to pivot between the initial position and the actuated position.

10. The surgical penetrating system according to claim 1, wherein at least one actuation link is slidably connected to the at least one penetrating member.

11. The surgical penetrating system according to claim 10, wherein the at least one actuation link is adapted to move the at least one penetrating member between the initial and actuated positions.

12. The surgical penetrating system according claim 1 including at least one actuation member disposed within the outer wall and operatively connected to the at least one penetrating member, the at least one actuation member adapted to translate relative to the longitudinal axis to move the at least one penetrating member between the initial position and the actuated position.

13. The surgical penetrating system according to claim 12 wherein the at least one actuation member is mounted within the at least one wall slot defined within the outer wall of the cannula and is adapted to traverse the wall slot to move the at least one penetrating member between the initial position and the actuated position.

14. The surgical penetrating system according to claim 13 wherein the at least one penetrating member and the at least one actuation member are operatively connected through a cam slot and a cam pin arrangement.

15. The surgical penetrating system according to claim 12 including a plurality of penetrating members pivotably attached to the outer wall of the cannula, and adapted to pivot between the initial position and the actuated position, each of the penetrating members having an actuation member operatively coupled thereto.

16. The surgical penetrating system according to claim 1 wherein the at least one penetrating member includes a blade.

17. A surgical penetrating system comprising:
    a cannula including an outer wall arranged about a longitudinal axis and having a longitudinal opening dimensioned for passage of a surgical instrument, the cannula defining leading and trailing ends, the outer wall including at least one wall slot defined therein; and
    at least one penetrating member directly mounted to the outer wall of the cannula, the at least one penetrating member including a leading end and a trailing end, the trailing end of the at least one penetrating member being pivotably connected within the outer wall of the cannula, the at least one penetrating member adapted to pivotably move within the at least one wall slot between an initial position and an actuated position, wherein in the actuated position the leading end of the at least one penetrating member extends through the at least one wall slot to facilitate passage of the cannula through tissue.

* * * * *